Figure 1:
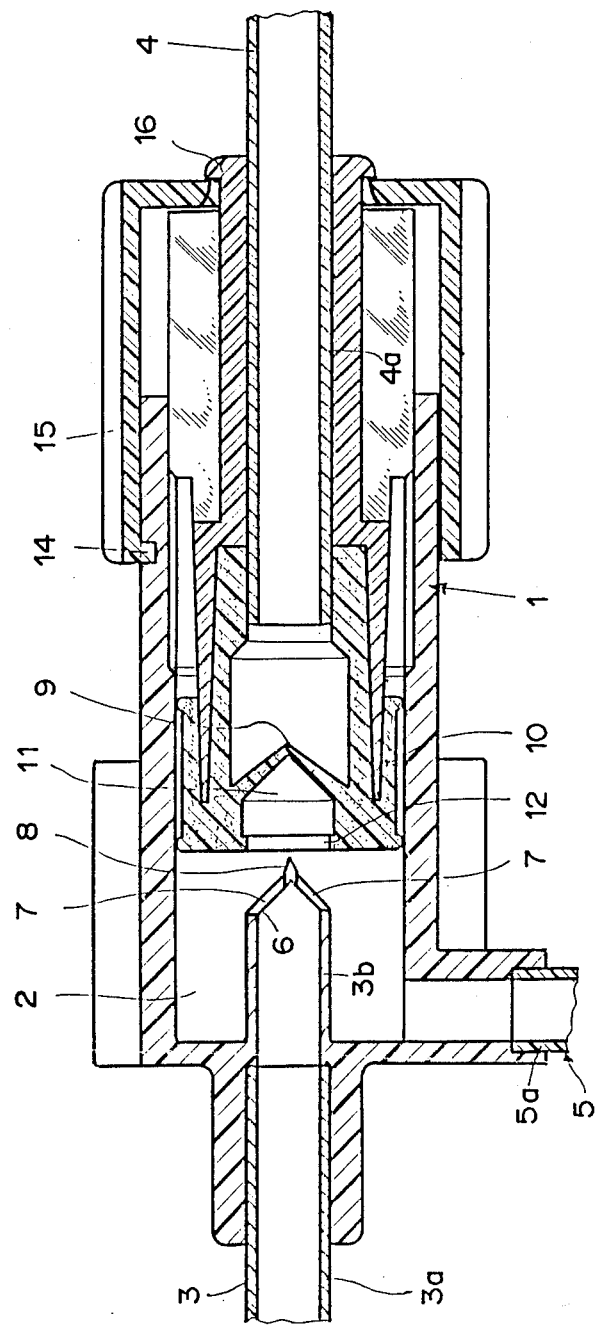

United States Patent [19]

Herrli

[11] Patent Number: 4,781,702

[45] Date of Patent: Nov. 1, 1988

[54] THREE-WAY CONNECTOR FOR LIQUID EXCHANGE

[75] Inventor: Peter Herrli, Biel, Switzerland

[73] Assignee: Contempo Products, P. Herrli, Biel, Switzerland

[21] Appl. No.: 63,180

[22] Filed: Jun. 16, 1987

[30] Foreign Application Priority Data

Jun. 20, 1986 [CH] Switzerland ............... 2506/86

[51] Int. Cl.⁴ .................................... A61M 5/245
[52] U.S. Cl. ........................ 604/244; 604/249;
604/284; 604/335; 604/905; 128/912; 137/625.49
[58] Field of Search ................ 604/27–30,
604/33, 43, 244, 246, 249, 256, 284, 335, 905,
283, 167, 169, 236; 128/766, 912; 137/625.48,
625.49, 625.68

[56] References Cited

U.S. PATENT DOCUMENTS

| | | |
|---|---|---|
| 3,513,849 | 5/1970 | Vaillancourt et al. ........... 604/256 |
| 4,106,491 | 8/1978 | Guerra .......................... 128/766 |
| 4,423,741 | 1/1984 | Levy .......................... 137/625.48 |
| 4,430,081 | 2/1984 | Timmermans ................... 604/167 |
| 4,457,749 | 7/1984 | Bellotti et al. ................... 604/29 |
| 4,496,348 | 1/1985 | Genese et al. ..................... 604/167 |
| 4,510,933 | 4/1985 | Wendt et al. .................... 604/167 |
| 4,655,762 | 4/1987 | Rogers .............................. 604/29 |

FOREIGN PATENT DOCUMENTS

WO84/03046 8/1984 PCT Int'l Appl. .

Primary Examiner—Stephen C. Pellegrino
Assistant Examiner—Ralph Lewis
Attorney, Agent, or Firm—Zarley, McKee, Thomte, Voorhees & Sease

[57] ABSTRACT

One end (4a) of a supply tube (4) opening out into the three-way connector is closed by a diaphragm (9) and filled with fresh fluid. This end is situated opposite one end of a duct (3b;36) to which a connection tube (3) is connected, with which it is axially aligned. This duct end has a pointed tip (8; 37) of hard plastic material. The end of the supply tube is axially displaceable in a chamber (2) of the three-way connector. By moving this end toward the tip of the duct end, the diaphragm is pierced by the tip, so that the fresh fluid can flow from the supply tube into the connection tube. One end of a drain tube (5) runs perpendicular to the duct end and opens out in the chamber. This closed three-way connector cannot be contaminated, is easy to use, and is largely proof against incorrect manipulation.

10 Claims, 6 Drawing Sheets

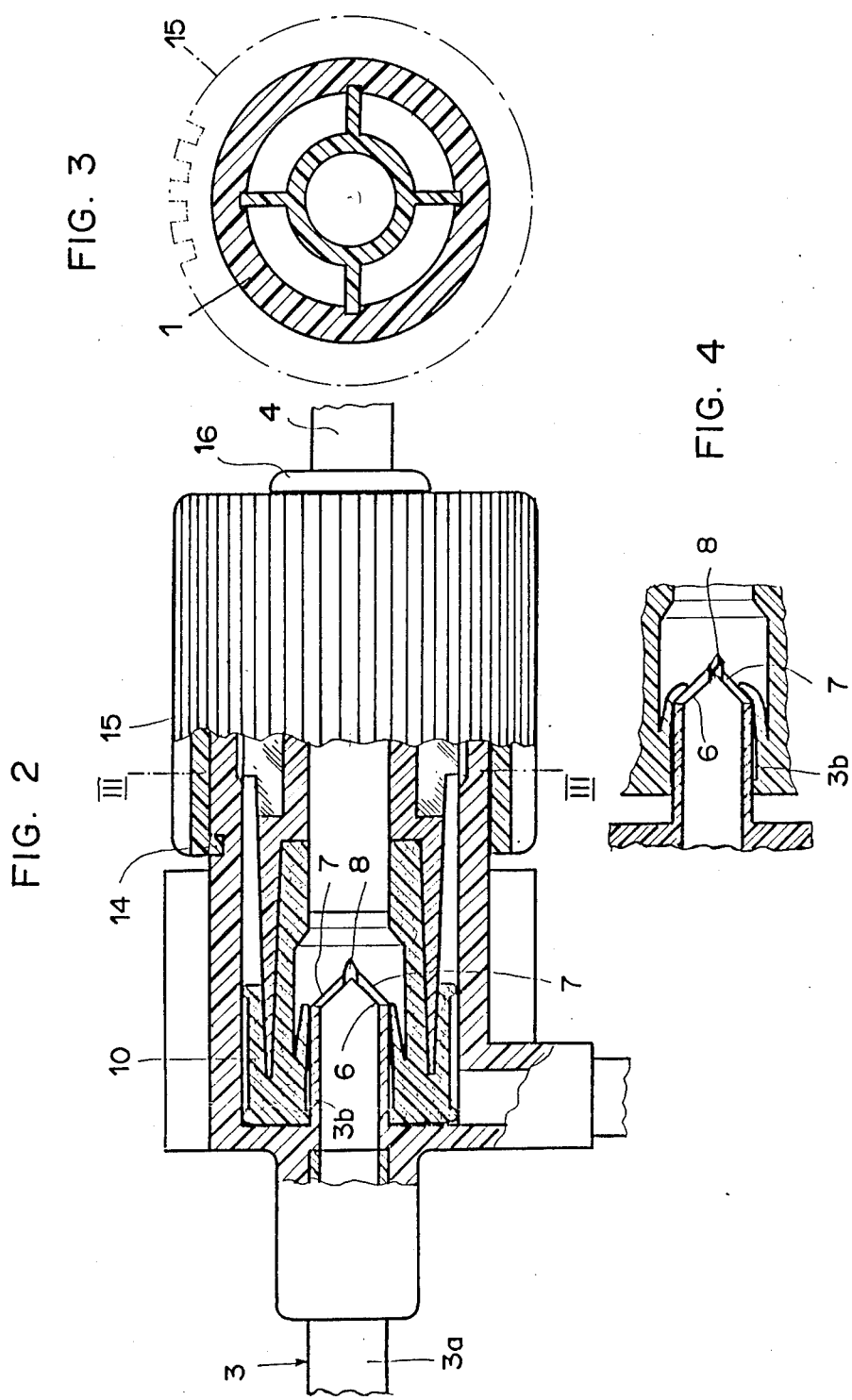

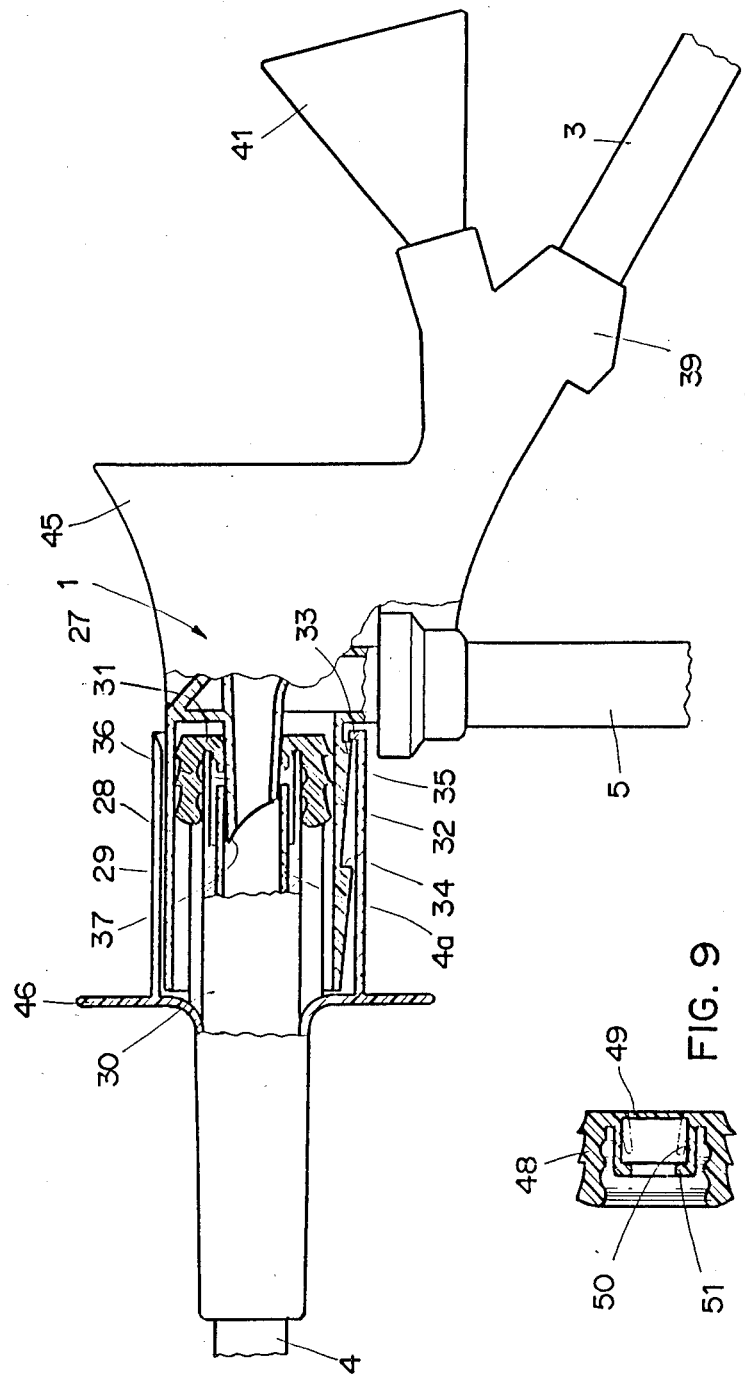

THREE-WAY CONNECTOR FOR LIQUID EXCHANGE

This invention relates to equipment for peritoneal dialysis, and more particularly to a three-way connector for the exchange of liquids, of the type in which a connection tube, a supply tube supplying fresh liquid, and a drain tube carrying off used liquid each terminate fluid-tightly at one end. The invention further relates to a peritoneal dialysis system utilizing the aforementioned connector.

Three-way connectors of this type are used especially in ambulatory systems in which metabolic products excreted by the damaged kidneys of a patient are dialytically withdrawn. In such cases, waste dialysis solution is withdrawn from the patient's peritoneal cavity, whereafter fresh dialysis solution is introduced into the cavity.

Continuous ambulatory peritoneal dialysis (CAPD) can be carried out by a kidney patient himself twenty-four hours a day and seven days a week, without interruption. Such home dialysis is performed in cycles of about six hours. The fresh solution to be introduced into the patient's peritoneal cavity has a volume of at least two liters. The waste solution is drained into an empty bag. By means of ambulatory dialysis, metabolic substances secreted by the patient's damaged kidneys are removed from his body, and during the exchange cycles he can go on with his usual daily activity.

When ambulatory peritoneal dialysis was first carried out, a system of bags was used which had to be worn by the patient at all times. In order to prevent the danger of contamination to a large extent, and to eliminate the discomfort of wearing the bags on the body, PCT Patent Publication No. WO 84/03046 discloses a Y-shaped junction for supplying the fresh dialysis solution from a bag and for draining the waste solution into a second bag. After the waste solution has been carried off, the tube leading to the bag holding it is clamped shut. A liquid disinfectant contained in the tube connected to the bag of fresh dialysis solution is used to rinse the Y-junction, or the Y-junction is flushed with fresh dialysis solution.

Here the technique of use is rather complicated. The patient must break off the spout of the bag of fresh dialysis solution and adjust the roller slide to regulate the rate of flow of the fresh solution. In addition, tube clamps must be used. Here too, however, the danger of contamination by germs still exists because such germs can propagate in the open Y-junction and particularly in the arm of the line intended for the flow of fresh solution. The Y-junction and the two bags are disposable, so that a new system of two bags and a Y-junction must be attached to the connection tube when the next dialysis takes place.

Although the foregoing apparatus permits the bag system to be detached, so that the patient no longer need carry the whole system about with him between changes of dialysis solution, it is so complicated to manipulate that only a selected group of patients can use it. With this apparatus, a wrong manipulation always represents a considerable risk of exogenous peritonitis.

It is an object of this invention to provide an improved three-way connector for liquid exchange which precludes the consequences of any contamination of the liquid flowing through it.

A further object of this invention is to provide such a connector, the use of which is simple, comfortable, and easy to learn.

Still another object of this invention is to provide such a connector with which incorrect manipulation is avoided by means of suitable safety measures and the exclusion of additional operating means.

To this end, in the three-way connector according to the present invention, of the type initially mentioned, the one end of the connection tube opens out into a tubular duct, there is a body having a chamber, in which body the one end of the supply tube and at least one end region of the duct are coaxially aligned, the one end of the drain tube opens out into the chamber, and the one end of the supply tube is closed, filled with the fresh liquid, and disposed axially displaceably in the chamber for the purpose of establishing a flow connection via the duct to the connection tube.

Also according to this invention, the three-way connector is utilized in a system for carrying out ambulatory peritoneal dialysis on patients having damaged kidneys.

Figure 5:
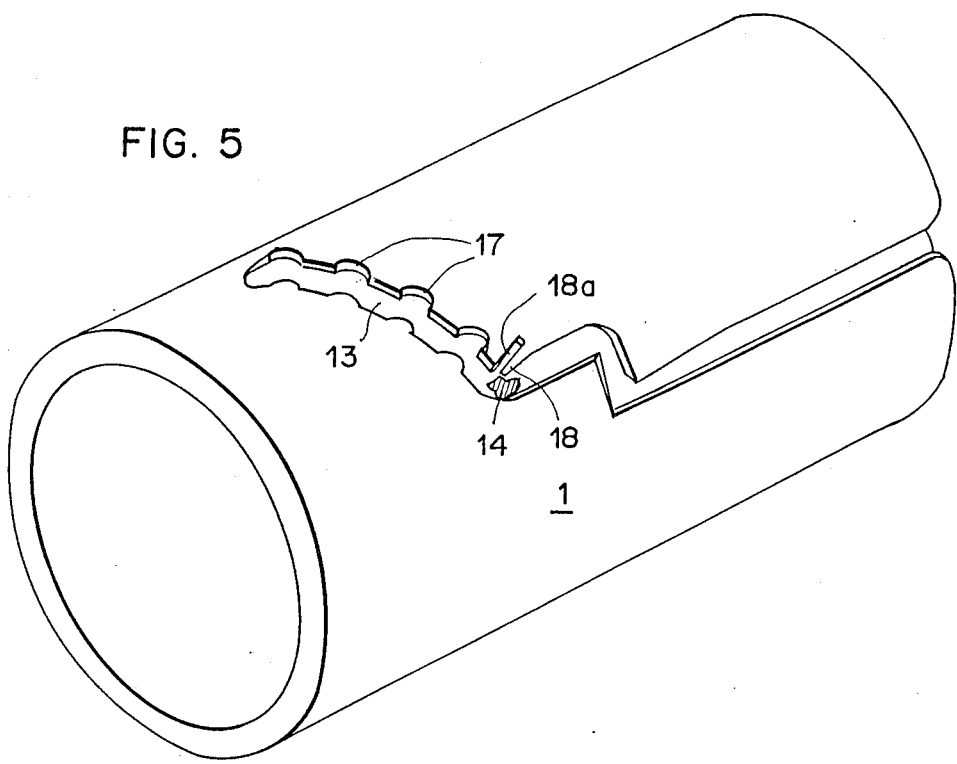
Figure 6:
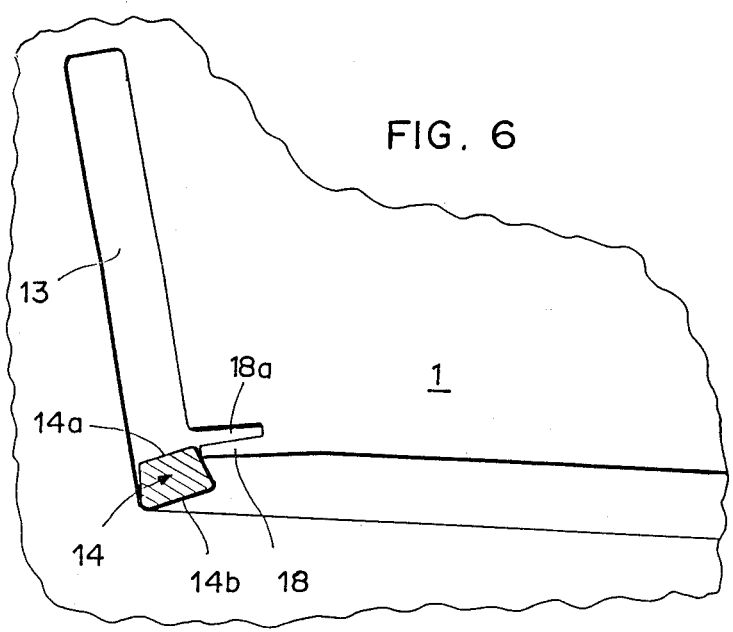
Figure 7:
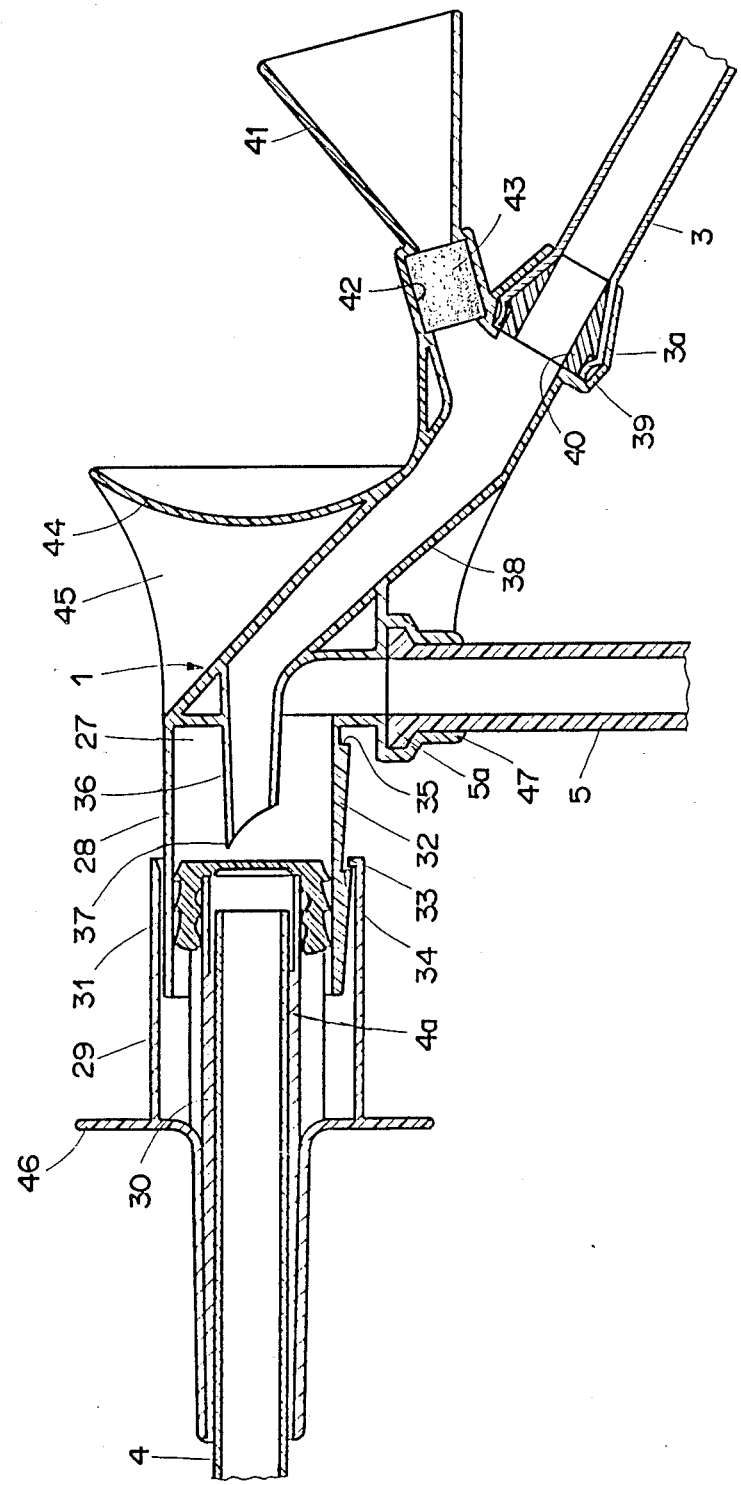
Figure 10:
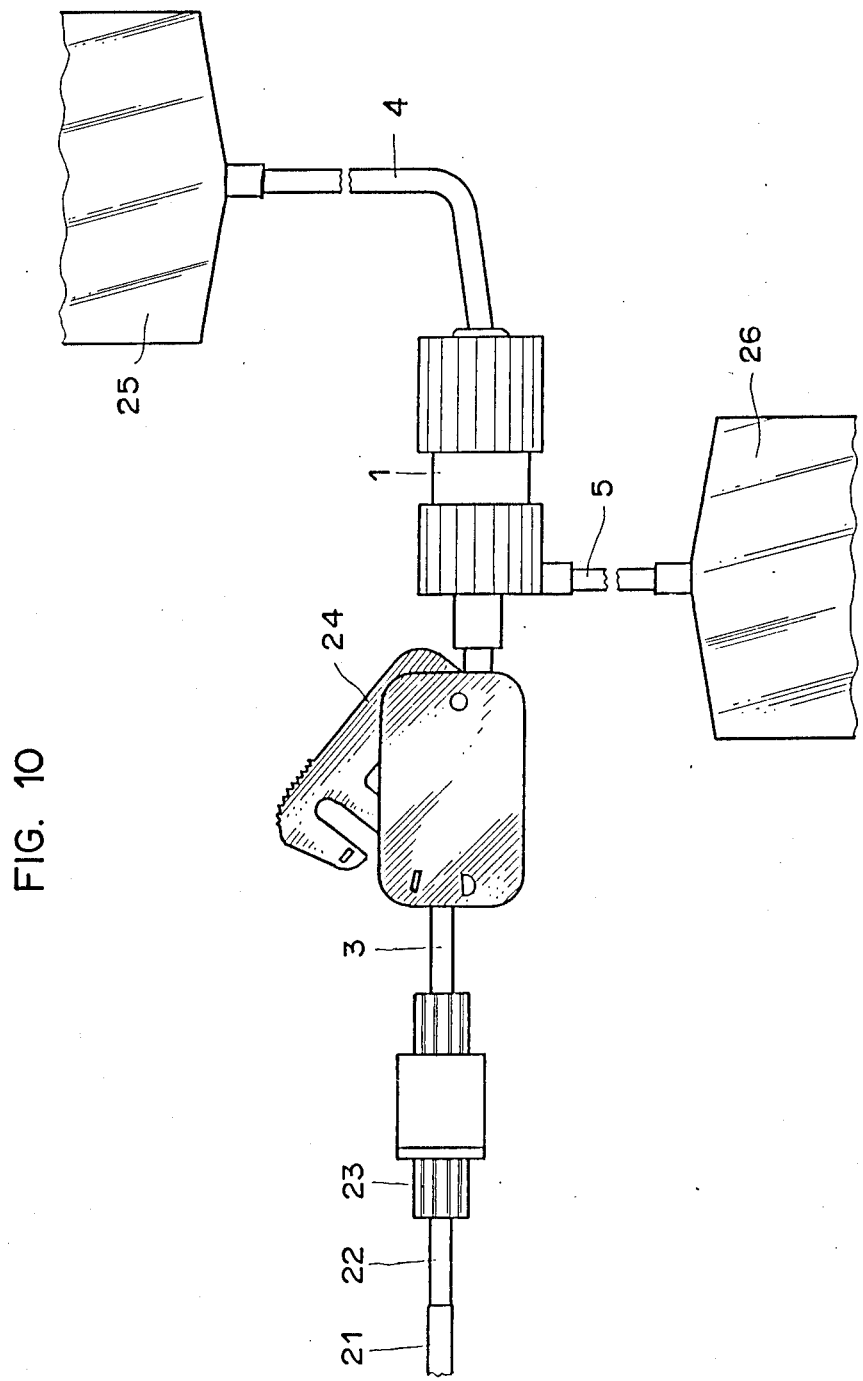

The invention will now be described in detail, by way of example, with reference to the accompanying drawings, in which:

FIG. 1 is a sectional view of a three-way connector for liquid exchange,

FIG. 2 is a sectional view of the three-way connector, showing a catch of a sliding sleeve engaging the outermost snap opening of a control groove, FIG. 3 is a section taken on the line III—III of FIG. 2, FIG. 4 is a sectional detail of the conical tip of the connection tube, by which a diaphragm of the supply tube has been pierced, FIG. 5 is a perspective view of the body of the three-way connector with the control groove, FIG. 6 is a developed view of the control groove of FIG. 5 with retraction-preventing means, FIG. 7 is a sectional view of another embodiment of the three-way connector, FIG. 8 is an elevation of the three-way connector of FIG. 7, partially in section, showing a diaphragm pierced by the tip of a tubular duct, FIG. 9 is a sectional view showing another form of the diaphragm, and FIG. 10 is a diagrammatic view of a system for carrying out ambulatory peritoneal dialysis.

The three-way connector shown in FIGS. 1-6, used for the exchange of liquids, may be utilized in various fields, particularly in a system for carrying out ambulatory peritoneal dialysis on patients having damaged kidneys. The three-way connector consists of a cylindrical body of plastic material in which there is a chamber 2. A connection tube 3, a supply tube 4 supplying fresh liquid, and a drain tube 5 carrying off waste liquid are each inserted fluid-tightly at one end into the body 1.

The one end 4a of the supply tube 4 is coaxially aligned with the one end 3a of the connection tube 3. The one end 5a of the drain tube 5 runs perpendicular to the end 3a of the connection tube 3 and opens out in the chamber 2. The end 3a of the connection tube 3 communicates with a tubular duct 3b comprising a cone 6 having apertures 7 and a pointed tip 8 of preferably hard plastic material or metal. The end 4a of the supply tube 4, situated opposite the tip 8, is closed by a diaphragm 9 and filled with the fresh liquid. For establishing a flow connection between the supply tube 4 and the connection tube 3 via the apertures 7 of the duct 3b, the end 4a of the supply tube 4 is disposed axially displaceably in the chamber 2. When the end 4a is displaced, the diaphragm 9 is moved toward the end 3a of the connection tube 3 and pierced by the tip 8 of the duct 3b.

A control groove 13 in the form of a helical line or a slide lock is made in the outside surface of the body 1 of the three-way connector. This outside surface is partially surrounded by a sliding sleeve 15. The sliding sleeve 15 has at one end a catch 14 which engages the control groove 13. The other end of the sliding sleeve 15 is fixed to a jacket 16 tightly surrounding the end 4a of the supply tube 4.

When the sliding sleeve 15 is rotated in one direction, its catch 14 will snap into various snap openings 17 of the control groove 13. Through rotation of the sliding sleeve 15, the end 4a of the supply tube 4 is pushed against the tip 8 of the connection tube 3 until the tip 8 pierces the diaphragm 9. The fresh liquid can then flow out of the supply tube 4, through the apertures 7 in the cone 6 of the duct 3b, and into connection tube 3. The flow of fresh liquid is graduated up to a maximum by moving the catch 14 step-wise into the farthest snap opening of the control groove 13. In this way, the rate of flow of the fresh liquid is controlled.

The development of the control curve 13 (FIG. 6) shows a means inserted for preventing retraction of the catch 14 engaging the groove 13. This safety measure may take the form of a slit 18a forming a resilient projection 18, for example. The safety means is situated at the point in the control groove 13 where the catch 14 will be situated when the diaphragm 9 is just in front of the tip 8. Instead, however, the front part 14a of the catch 14, inserted in the control groove 13, may be so designed that it tapers in cross-section relative to the rear part 14b of the catch 14. As the two parallel walls of the control groove 13 are resiliently yielding (the body 1 being made of plastic material), retraction of the catch 14 is prevented by means of its wide rear part 14b and the resiliently yielding parallel walls of the control groove 13.

When the end 4a of supply tube 4 has not been displaced, the apertures 7 in the cone 6 of the duct 3b attached to the connection tube 3 communicate with the chamber 2. In this phase, the waste liquid can flow out through the apertures 7 into the chamber 2 and be carried off through the drain tube 5.

The end 4a of the supply tube 4 is enclosed in an appendage 10, preferably of soft plastic material. The projecting free end portion of the appendage 10 has in the center a recess 11, matching the shape of the tip 8 of the cone 6 of the connection tube 3 and closed by the diaphragm 9. The entry rim of the recess 1 is provided with a sealing lip 12. When the end 4a of the supply tube 4 is moved toward the connection tube tip 8, this tip first enters the recess 11, after which the diaphragm 9 is pierced. This phase occurs when the catch 14 snaps into the farthest snap opening 17 of the control groove 13. In this phase, the chamber 2 of the body 1 is completely and sealingly occupied by the appendage 10, so that any air which may have penetrated there previously is forced into the drain tube 5, and inlet opening of the drain tube 5 into the chamber 2 is sealed off.

FIGS. 7 and 8 show a further embodiment of a three-way connector, in section and partially in section, respectively. Only the completely identical parts, such as the connection tube 3, the supply tube 4, and the drain tube 5, as well as the ends 3a, 4a, and 5a of these tubes, are designated by the same reference numerals as in the embodiment of FIGS. 1–6.

A partially cylindrical body 28 chiefly bounding a chamber 27 is preferably made of plastics. Mounted on the cylindrical portion of the body 28 is a sliding sleeve 29 into which a jacket 30 tightly enclosing the end 4a projects. The inner end of the jacket 30 is closed by a diaphragm 31. The thickened cylindrical rim 32 of the diaphragm 31 has both inside and outside annular ribs which rest sealingly against the jacket 30 on one side and against the inside of the cylindrical portion of the body 28 on the other side. The end 4a of the supply tube 4 enclosed by the jacket 30 is cemented in this jacket and thus firmly fixed to it. At the inner end of the jacket 30, its inside diameter increases, and part of the end 4 of the supply tube 4 projects into this widened portion of the jacket 30.

Disposed at one location on the cylindrical portion of the body 28 is an axially extending rib 32 which projects radially outward and is, viewed in cross-section, of a sawtooth shape. In the region of the rib 32, the sliding sleeve 29 has a rim 33 projecting radially inward for engaging behind radially extending shoulders 34 and 35 of the sawtooth-shaped rib 32. The shoulders 34 and 35 keep the sliding sleeve 29 from moving toward the left, as viewed in FIGS. 7 and 8, when the rim 33 has engaged behind one or the other of the shoulders 34, 35.

A tube attachment 36, disposed coaxially with the jacket 30 of the sliding sleeve 29 and forming part of a tubular duct, projects into the chamber 27. The end of the attachment 36 opening out into the chamber 27 is chamfered and forms a pointed tip 37 for piercing the diaphragm 31 when the sliding sleeve 29 is moved from the position shown in FIG. 7 to that shown in FIG. 8.

The tube attachment 36 is connected to a coupling 39 by means of a tube piece 38 disposed at an angle to the longitudinal axis of the sliding sleeve 29. The end 3a of the connection tube 3 is fluid-tightly clamped into the coupling 39 by means of a conical socket 40. Just beside the coupling 39, a funnel 41 opens into the tube piece 38 via a passage 42. Disposed in the passage 42 between the tube piece 38 and the funnel 41 is a stopper 43 of an elastic material. The stopper 43 can be pierced by the needle of a hypodermic (not shown) for injecting medication into the tube piece 38. The purpose of the funnel 41 is to facilitate introduction of the hypodermic. The stopper 43 closes by itself after the needle is withdrawn.

From the mid-region on the tube piece 38 there extends a curved wall 44, intended as a thumb-rest, which is connected to the remainder of the tube piece 38 by a support wall 45. The sliding sleeve 39 comprises a flange 46 projecting radially outward and intended as a rest for the index and middle fingers of the person using the three-way connector. When the thumb is placed on the curved wall 44 and the two fingers beneath the flange 46, the sliding sleeve 29 can easily be moved from the position shown in FIG. 7 to that shown in FIG. 8.

The chamber 27 communicates with the end 5a of the drain tube 5 via a connection piece 47. The thickened rim of the end 5a is held form-lockingly by the connection piece 47.

The sliding sleeve 29, the tube attachment 36, the tube piece 38, the coupling 39, the funnel 41, and the wall 44 are preferably made of a plastic material and are initially produced as two half-shells, the sectional plane of FIGS. 7 and 8 being the plane of separation of the two half-shells. After the end 3a of the connection tube 3 is provided with the socket 40 and inserted in the divided coupling 39, the stopper 43 is inserted in the divided passage 42 between the tube piece 38 and the funnel 41, and the widened rim of the end 5a of the drain tube 5 is inserted into the divided connection piece 47, the other half-shell is placed upon the first one and welded to it along the plane of separation. The sliding sleeve 29, together with the end 4a of the supply tube 4 cemented in its jacket 30, is then pushed over the cylindrical portion of the body 28 until the rim 33 engages behind the first shoulder 34 of the rib 32.

The outside diameter of the end of the tube attachment 36 projecting into the chamber 27 is substantially the same as the inside diameter of the end 4a of the supply tube 4. The outside diameter of the tube attachment 36 increases slightly toward the tube piece 38, so that in the position of the sliding sleeve 29 shown in FIG. 8, the end 4a of the elastic supply tube 4 is expanded somewhat. This is made possible by the widened inside diameter of the jacket 30 at its inner end and brings about an absolutely fluid-tight connection between the end 4a and the tube attachment 36. At the same time, the connection between the drain tube 5 and the two other tubes 3 and 4 is completely cut off.

FIG. 9 shows a section through a preferred form of the diaphragm 31 depicted in FIGS. 7 and 8. A portion 48 of a modified diaphragm 49 surrounding the jacket 30 likewise includes ribs projecting radially outward and inward. Disposed coaxially with the portion 48 is a tubular projection 50 having a bead 51 protruding radially inward at its free end. The modified diaphragm 49 is used when only a short end section of the supply tube 4 extends into the jacket 30 and the inside diameter of the jacket 30 is uniform over its entire length. The inside end of the jacket 30 is situated between the portion 48 and the tubular projection 50. When the tube attachment 36 has pierced the diaphragm 49, the bead 51 rests against the attachment 36 and forms a gasket which prevents contaminants from reaching the supply tube 4 from the chamber 27. Moreover, the remnants of the pierced diaphragm 49 can accumulate in the annular space between the tube attachment 36 and the tubular projection 50.

FIG. 10 illustrates a system for carrying out ambulatory peritoneal dialysis on patients having damaged kidneys, utilizing the three-way connector of FIG. 1. FIG. 9 shows a catheter 21 inserted in the patient's peritoneal cavity, a catheter extension 22, a closure 23, the connection tube 3, a device 24 for clamping and severing the connection tube 3, the body 1 of the three-way connector, the supply tube 4 for supplying the fresh dialysis solution from a bag 25, and the drain tube 5 for draining the waste liquid into a bag 26. The metabolic products excreted by the patient's damaged kidneys are carried off from the patient's peritoneal cavity by the waste solution, whereupon fresh dialysis solution is introduced into the patient's peritoneal cavity. Such a dialysis can be carried out by the patient himself, e.g., at home.

The three-way connectors described above each represent a completely closed, i.e., sealed, unit having clearly defined flow routes for the liquids. Their operation is limited to twisting and thus sliding the sliding sleeve on the body of the three-way connector and snapping the catch of that sliding sleeve into the corresponding snap openings of the control groove. The liquids always flow through the three-way connector in only one direction, and the fresh liquid does not come in contact with the waste liquid. The time-consuming and troublesome rinsing-out operation of the prior art, always presenting a certain risk of contamination, is unnecessary.

I claim:

1. A three-way connector for the exchange of fluids, of the type having a valve body, a connection tube, a supply tube, a drain tube, and means for holding one end of each of the tubes in the valve body, wherein the improvement comprises:
    a chamber defined by said valve body, said one end of said connection tube and of said drain tube opening out into said chamber;
    a tubular duct extending from said correction tube having an end projecting into said chamber and axially aligned with said one end of said supply tube;
    a diaphragm closing said one end of said supply tube; and means for axially displacing said one end of said supply tube between a first position wherein said end of said supply tube is remote from said end of said tubular duct and said connection tube communicates with said drain tube for fluid exchange, and a second position wherein said one end of said supply tube is in proximity to said end of said tubular duct and said diaphragm is pierced by said end of said tubular duct, thereby establishing communication between said supply tube and said connection tube.

2. The three-way connector of claim 1, wherein said end of said duct comprising a cone having a plurality of apertures and a pointed tip of a hard material.

3. The three-way connector of claim 2, further comprising an appendage of soft material enclosing said one end of said supply tube and having a projecting end portion remote therefrom, said end portion including a central recess matching said cone, said recess being closed by said diaphragm and having a rim provided with a sealing lip.

4. The three-way connector of claim 3, wherein in the fully displaced state of said one end of said supply tube, said one end of said drain tube opening out into said chamber is fluid-tightly closed by said appendage.

5. The three-way connector of claim 2, wherein said body includes in the outside surface thereof a helical groove having snap openings, further comprising a sliding sleeve partially surrounding said body and including a catch engaging said groove, a jacket tightly surrounding said one end of said supply tube, and means disposed in said groove for preventing retraction of said catch, said sliding sleeve being fixed to said jacket, and said catch co-operating with said snap openings of said groove to form a control means for controlling the rate of flow of fluid through said apertures.

6. The three-way connector of claim 1, wherein said end of said duct is chamfered to form a pointed tip.

7. The three-way connector of claim 6, comprising means for axially displacing said one end of said supply tube toward said end region of said duct for causing said diaphragm to be pierced by said pointed tip.

8. The three-way connector of claim 6, wherein said body further comprises a tube piece adjoining said duct at an angle to the longitudinal direction thereof and including at the end thereof remote from said duct a conical clamping socket for receiving said one end of said connection tube, a passage portion situated adjacent to said socket, and a funnel joined to said passage portion, said connector further comprising a resilient stopper disposed in said passage portion.

9. The three-way connector 8, wherein said tube piece includes a wall portion situated substantially in the center thereof and intended to serve as a thumb-rest for a user of said connector, said sliding sleeve having a flange projecting radially therefrom and intended to serve as a rest for the index and middle fingers of a said user.

10. The three-way connector of claim 6, wherein said chamber is partially bounded by a cylindrical portion of said body, further comprising a sliding sleeve disposed over said cylindrical portion of said body and displaceable from a first position to a second position, and a jacket substantially surrounded by said sliding sleeve, said one end of said supply tube being fixed in said jacket by means of an adhesive.

* * * * *